United States Patent
Langley et al.

(10) Patent No.: US 6,949,082 B2
(45) Date of Patent: Sep. 27, 2005

(54) DOSING MEANS FOR AN INJECTION DEVICE

(75) Inventors: Christopher Nigel Langley, Warwickshire (GB); Shane Alistair Day, Warwick (GB); Robert Frederick Veasey, Leamington Spa (GB); Robert Woolston, Warwick (GB)

(73) Assignee: Lea Design International Limited, Warwick (GB)

( * ) Notice: Subject to any disclaimer, the term of this patent is extended or adjusted under 35 U.S.C. 154(b) by 0 days.

(21) Appl. No.: 10/433,905

(22) PCT Filed: Dec. 21, 2001

(86) PCT No.: PCT/GB01/05721

§ 371 (c)(1),
(2), (4) Date: Dec. 5, 2003

(87) PCT Pub. No.: WO02/051473

PCT Pub. Date: Jul. 4, 2002

(65) Prior Publication Data

US 2004/0073173 A1 Apr. 15, 2004

(30) Foreign Application Priority Data

Dec. 22, 2000 (GB) .............................................. 0031466

(51) Int. Cl.[7] ............................................. A61M 31/00
(52) U.S. Cl. ........................................................ 604/67
(58) Field of Search ............................ 604/65, 154, 66, 604/189, 67, 207, 208, 209, 211; 128/DIG. 12, DIG. 13, DIG. 1

(56) References Cited

U.S. PATENT DOCUMENTS

| | | | | |
|---|---|---|---|---|
| 4,925,444 A | * | 5/1990 | Orkin et al. | 604/80 |
| 4,976,696 A | | 12/1990 | Sanderson et al. | |
| 5,041,086 A | * | 8/1991 | Koenig et al. | 604/65 |
| 5,207,642 A | * | 5/1993 | Orkin et al. | 604/65 |
| 5,536,249 A | * | 7/1996 | Castellano et al. | 604/65 |
| 5,593,390 A | * | 1/1997 | Castellano et al. | 604/187 |
| 5,925,021 A | * | 7/1999 | Castellano et al. | 604/207 |
| 6,551,276 B1 | * | 4/2003 | Mann et al. | 604/131 |
| 6,558,351 B1 | * | 5/2003 | Steil et al. | 604/131 |

FOREIGN PATENT DOCUMENTS

| | | |
|---|---|---|
| EP | 0 293 958 A1 | 12/1988 |
| EP | 0 980 688 A2 | 2/2000 |
| GB | 2 094 628 A | 9/1982 |
| WO | WO 97/21456 | 6/1997 |

* cited by examiner

Primary Examiner—Manuel Mendez
(74) Attorney, Agent, or Firm—Oliff & Berridge, PLC

(57) ABSTRACT

A medicament delivery device is disclosed having dose dial means 6,8 to determine a quantity of medicament to be delivered. The medicament delivery device is also provided with selection means to select whether the quantity of medicament to be delivered is determined as a multiple of a first quantum of units or as a multiple of a second quantum of units.

5 Claims, 2 Drawing Sheets

DOSING MEANS FOR AN INJECTION DEVICE

The present invention relates to a medicament delivery device, and in particular, to medicament delivery devices adapted for self-administration of a medicament by a patient. Such devices have particular, but not exclusive, application in the treatment of diabetes.

Medicament delivery devices include infusion devices and pen-type injectors. Such medicament delivery devices typically expel measured amounts of a medicament from a replaceable medicament cartridge. The medicament delivery device conveniently includes means to select a desired quantity of medicament to be delivered.

In known medicament delivery devices, dependant upon the need of the patient, the quantity of medicament can be selected as a multiple of whole units in some injectors or as a multiple of half units in other injectors. This presents a degree of inflexibility in the operation of such medicament delivery devices.

It is an advantage of the present invention that it eliminates this problem.

According to a first aspect of the present invention, a medicament delivery device comprising dose dial means to determine a quantity of medicament to be delivered is also provided with selection means to select whether the quantity of medicament to be delivered is determined as a multiple of a first quantum of units or as a multiple of a second quantum of units.

Preferably, the first quantum of units is whole units and the second quantum of units are half units.

Preferably, the selection means comprises a switch or a combination of switches to be actuated by a user.

Alternatively, the medicament delivery device further comprises a microprocessor and a display in which the selection means comprises an option provided on the display to be selected by a user.

Preferably, the medicament delivery device incorporates means to display to a user whether the selection means is operative to cause the dose dial means to determine the quantity of medicament to be delivered as a multiple of a first quantum of units or as a multiple of a second quantum of units.

The invention will now be described, by way of example only, with reference to the accompanying drawings, in which.

Figure 1:
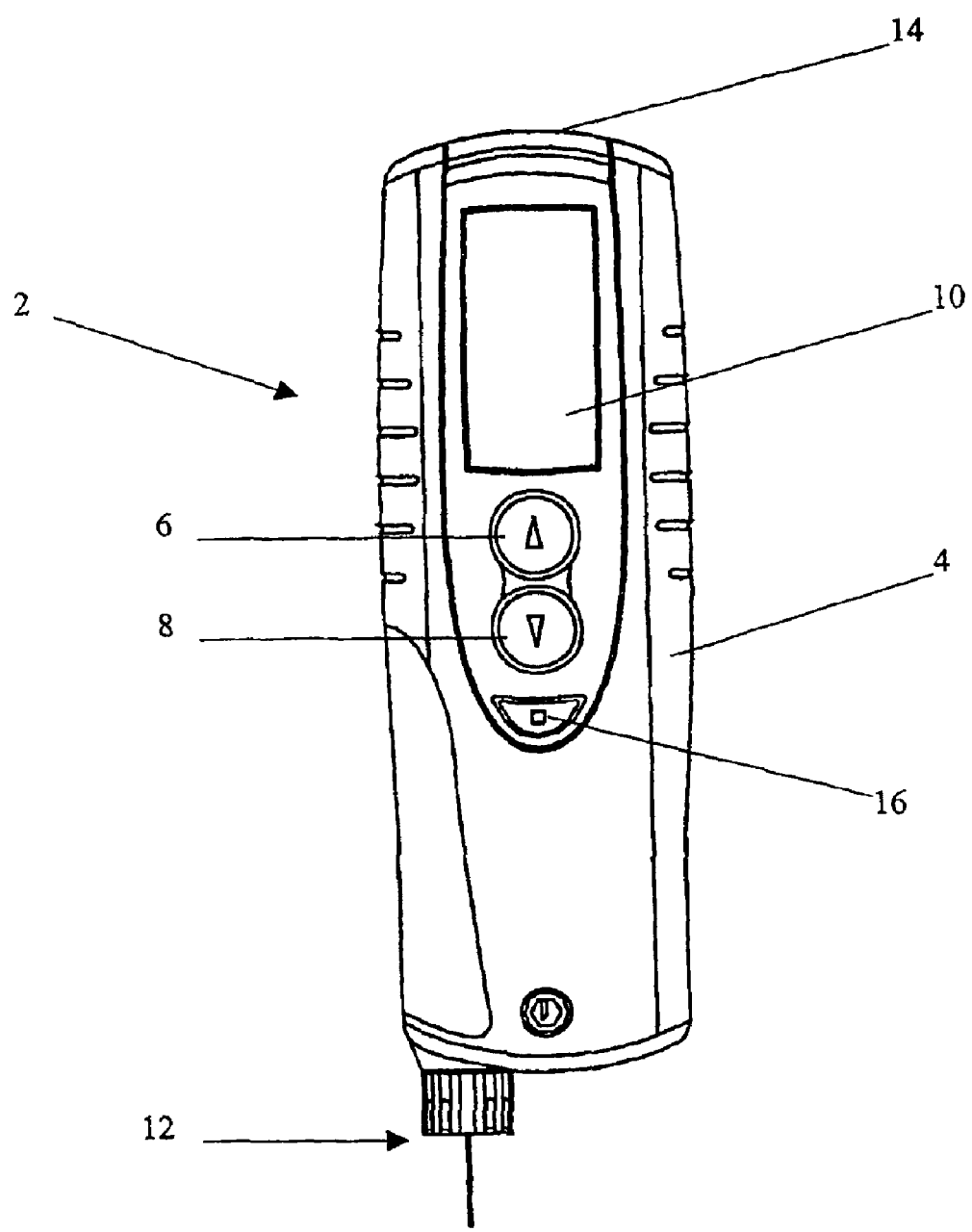
FIG. 1 shows a plan view of a medicament delivery device incorporating the present invention.

Referring to FIG. 1 there is shown a plan view of a medication delivery device, in the illustrated embodiment a pen-type injector 2. The injector 2 can be seen to comprise a main housing 4 about which are incorporated dose dial means 6,8, a display 10, a needle unit 12, and a dose delivery button 14. The display is adapted to communicate information to a user, such as the amount of medicament selected to be injected.

A user operates the medicament delivery device by manipulating the dose dial means 6,8 to select a desired quantity of medicament to be injected. This quantity may then be confirmed by pressing a dose confirmation button 16. Upon operation of the dose delivery button 14, a microprocessor 20 causes a drive means 22 within the housing 4 to operate to expel the desired quantity of medicament.

The dose dial means 6,8 conveniently comprises two buttons, one to increase the amount of medicament to be delivered, the other to decrease the amount of medicament to be delivered. In each case a single depression of each button will cause the amount of medicament to be altered by a unit; a whole unit or a half unit depending upon the mode of operation. The medicament delivery device may be adapted such that holding each of the buttons down will cause continued alteration of the dose being dialed.

Figure 2:
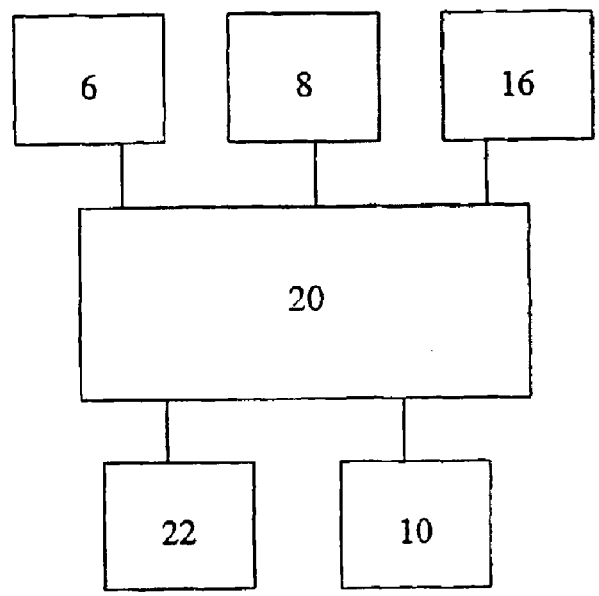
FIG. 2 shows a somewhat schematically a first control arrangement for the operation of the delivery device in accordance with the present invention.

In the embodiment illustrated in FIG. 2, selection of the mode of operation may be changed between part unit alteration to whole unit alteration by causing both of the dose dial buttons 6,8 to be depressed simultaneously.

The display 10 may also be adapted to communicate to the user whether the selection means is operative to cause the dose dial means 6,8 to determine the quantity of medicament to be delivered as a multiple of whole units or as a multiple of part units.

Figure 3:
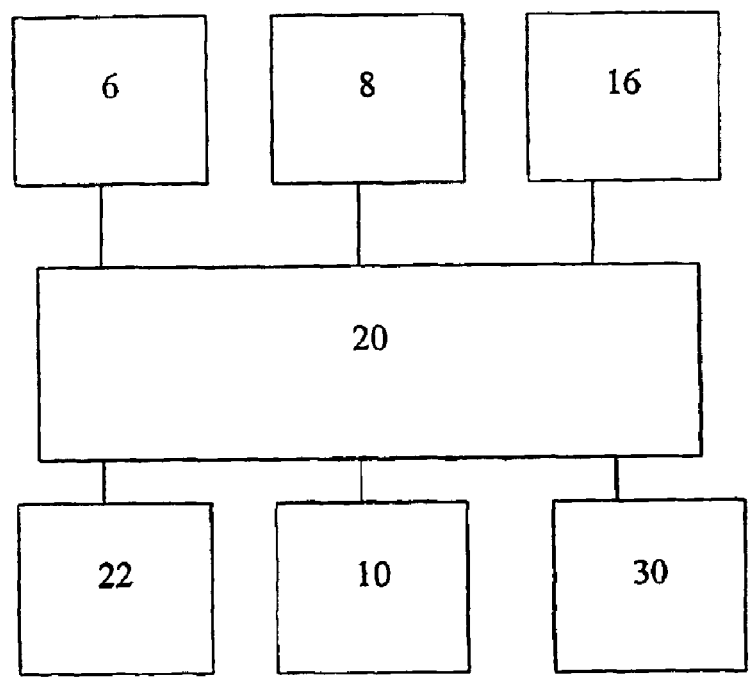
FIG. 3 shows a somewhat schematically a second control arrangement for the operation of the delivery device in accordance with the present invention.

In the embodiment of FIG. 3 in which like reference numerals refer to like parts, the selection means comprises an additional dedicated button 30.

In one embodiment of the present invention, the selection means may only be operated once during a predetermined period during the product life of the medicament delivery device. This prevents accidental operation of the selection means beyond this predetermined period.

In a further embodiment, the selection means may, additionally or alternatively, only be operated by the manufacturer such that the quantum of units used to determine the quantity of medicament to be delivered is chosen before the user is in possession of the device. This conveniently occurs as part of the manufacturing process. This enables a variety of medicament delivery devices having different operating configurations to be produced along a single manufacturing line.

What is claimed is:

1. A medicament delivery device for self administration of a medicament by a patient comprising a dose dial means to determine a quantity of medicament to be delivered is characterised in that the device is further provided with selection means to select whether the quantity of medicament to be delivered is determined as a multiple of a first quantum of units or as a multiple of a second quantum of units and in which the selection means may only be operated once during a predetermined period during product life of the medicament delivery device.

2. A medicament delivery device according to claim 1, in which the first quantum of units is whole units and the second quantum of units are half units.

3. A medicament delivery device according to claim 1, in which the medicament delivery device further comprises a microprocessor 20 and a display 10 in which the selection means comprises an option provided on the display 10 to be displayed.

4. A medicament delivery device according to claim 1, in which one of the first or second quantum of units are half units.

5. A medicament delivery device according to claim 1, in which the selection means may only be operated by a manufacturer such that the quantum of units used to determine the quantity of medicament to be delivered is chosen before a user is in possession of the device.

* * * * *

UNITED STATES PATENT AND TRADEMARK OFFICE
CERTIFICATE OF CORRECTION

PATENT NO. : 6,949,082 B2 Page 1 of 1
DATED : September 27, 2005
INVENTOR(S) : Christopher Nigel Langley et al.

It is certified that error appears in the above-identified patent and that said Letters Patent is hereby corrected as shown below:

<u>Title page,</u>
Item [73], Assignee, change " Lea Design International Limited" to -- DCA Design International Limited --.

Signed and Sealed this

Twenty-third Day of May, 2006

JON W. DUDAS
*Director of the United States Patent and Trademark Office*